United States Patent
Edwards

(10) Patent No.: US 10,433,761 B2
(45) Date of Patent: Oct. 8, 2019

(54) METHODS FOR LOCALIZING MEDICAL INSTRUMENTS DURING CARDIOVASCULAR MEDICAL PROCEDURES

(71) Applicant: CardioNXT, Inc., Westminster, CO (US)

(72) Inventor: Jerome Ranjeev Edwards, Erie, CO (US)

(73) Assignee: CardioNXT, Inc., Westminster, CO (US)

( * ) Notice: Subject to any disclaimer, the term of this patent is extended or adjusted under 35 U.S.C. 154(b) by 58 days.

(21) Appl. No.: 15/369,183

(22) Filed: Dec. 5, 2016

(65) Prior Publication Data

US 2017/0303816 A1 Oct. 26, 2017

Related U.S. Application Data

(63) Continuation of application No. 13/747,266, filed on Jan. 22, 2013, now Pat. No. 9,510,772.

(Continued)

(51) Int. Cl.
*A61B 5/00* (2006.01)
*A61B 5/06* (2006.01)
(Continued)

(52) U.S. Cl.
CPC ............. *A61B 5/061* (2013.01); *A61B 5/063* (2013.01); *A61B 34/20* (2016.02); *A61B 5/6869* (2013.01);
(Continued)

(58) Field of Classification Search
CPC . A61B 34/20; A61B 5/061; A61B 2034/2072; A61B 2034/2051;
(Continued)

(56) References Cited

U.S. PATENT DOCUMENTS

| 5,391,199 A | 2/1995 | Ben-Haim |
| 5,433,489 A | 7/1995 | Kimura et al. |

(Continued)

FOREIGN PATENT DOCUMENTS

| CN | 201759559 | 3/2011 |
| DE | 3908797 A1 | 9/1990 |

(Continued)

OTHER PUBLICATIONS

Extended European Search Report for European Application No. 13775770.4, dated Mar. 4, 2016.

(Continued)

*Primary Examiner* — Aaron B Fairchild
(74) *Attorney, Agent, or Firm* — Cooley LLP

(57) ABSTRACT

A system and method for localizing medical instruments during cardiovascular medical procedures is described. One embodiment comprises an electromagnetic field generator; an antenna reference instrument adapted to be introduced into the heart of a subject and including at least one electromagnetic sensor and at least one electrode; at least one roving instrument adapted to be introduced into the thorax cavity of the subject and including at least one electrode; and a control unit configured to determine position coordinates of the antenna reference instrument based on an electromagnetic signal from the electromagnetic field generator sensed by the electromagnetic sensor, measure an electrical-potential difference between the electrode of the antenna reference instrument and the electrode of the roving instrument, and calibrate the measured electrical-potential difference using the determined position coordinates of the antenna reference instrument to determine position coordinates of the roving instrument.

14 Claims, 8 Drawing Sheets

Related U.S. Application Data

(60) Provisional application No. 61/622,220, filed on Apr. 10, 2012.

(51) Int. Cl.
*A61B 34/20* (2016.01)
*A61M 25/01* (2006.01)

(52) U.S. Cl.
CPC ............. *A61B 2034/2051* (2016.02); *A61B 2034/2053* (2016.02); *A61B 2034/2072* (2016.02); *A61B 2560/0223* (2013.01); *A61M 2025/0166* (2013.01)

(58) Field of Classification Search
CPC ... A61B 2034/2053; A61B 2560/0223; A61M 2025/0166
See application file for complete search history.

(56) References Cited

U.S. PATENT DOCUMENTS

| | | |
|---|---|---|
| 5,545,204 A | 8/1996 | Cammilli et al. |
| 5,697,377 A | 12/1997 | Wittkampf |
| 5,729,129 A | 3/1998 | Acker |
| 5,913,820 A | 6/1999 | Bladen et al. |
| 5,983,126 A | 11/1999 | Wittkampf |
| 6,172,499 B1 | 1/2001 | Ashe |
| 6,177,792 B1 | 1/2001 | Govari et al. |
| 6,233,476 B1 | 5/2001 | Strommer et al. |
| 6,292,690 B1 | 9/2001 | Petrucelli et al. |
| 6,400,139 B1 | 6/2002 | Khalfin et al. |
| 6,522,907 B1 | 2/2003 | Bladen et al. |
| 6,569,160 B1 | 5/2003 | Goldin et al. |
| 6,574,498 B1 | 6/2003 | Gilboa |
| 6,690,963 B2 | 2/2004 | Ben-Haim et al. |
| 6,788,967 B2 | 9/2004 | Ben-Haim et al. |
| 7,263,397 B2 | 8/2007 | Hauck et al. |
| 7,266,408 B2 | 9/2007 | Bojovic et al. |
| 7,536,218 B2 | 5/2009 | Govari et al. |
| 7,684,850 B2 | 3/2010 | Govari et al. |
| 7,848,789 B2 | 12/2010 | Govari et al. |
| 8,046,052 B2 | 10/2011 | Verard et al. |
| 8,137,343 B2 | 3/2012 | Harlev et al. |
| 8,167,876 B2 | 5/2012 | Harlev et al. |
| 8,175,681 B2 | 5/2012 | Hartmann et al. |
| 8,185,192 B2 | 5/2012 | Markowitz et al. |
| 8,401,616 B2 | 3/2013 | Verard et al. |
| 8,401,625 B2 | 3/2013 | Harlev et al. |
| 8,494,614 B2 | 7/2013 | Markowitz et al. |
| 9,218,687 B2 | 12/2015 | Hill et al. |
| 9,510,772 B2 | 12/2016 | Edwards |
| 2002/0030483 A1 | 3/2002 | Gilboa |
| 2004/0015194 A1 | 1/2004 | Ransbury |
| 2004/0097805 A1 | 5/2004 | Verard et al. |
| 2006/0173269 A1 | 8/2006 | Glossop |
| 2006/0235476 A1 | 10/2006 | Gunderson et al. |
| 2007/0016007 A1 | 1/2007 | Govari et al. |
| 2007/0159488 A1 | 7/2007 | Danskin et al. |
| 2008/0058657 A1 | 3/2008 | Schwartz et al. |
| 2008/0146954 A1 | 6/2008 | Bojovic et al. |
| 2008/0161681 A1 | 7/2008 | Hauck |
| 2008/0287769 A1 | 11/2008 | Kurzweil et al. |
| 2009/0027403 A1 | 1/2009 | Jung |
| 2009/0264748 A1 | 10/2009 | Markowitz et al. |
| 2010/0152571 A1 | 6/2010 | Hartmann et al. |
| 2010/0168560 A1 | 7/2010 | Hauck et al. |
| 2010/0168735 A1 | 7/2010 | Deno et al. |
| 2011/0144509 A1 | 6/2011 | Kahlert et al. |
| 2011/0230775 A1 | 9/2011 | Barley et al. |
| 2011/0288605 A1 | 11/2011 | Kaib et al. |
| 2012/0197243 A1 | 8/2012 | Sherman et al. |
| 2012/0209343 A1 | 8/2012 | Efimov et al. |
| 2013/0267835 A1 | 10/2013 | Edwards |
| 2013/0274593 A1 | 10/2013 | Everling |
| 2014/0107430 A1 | 4/2014 | Deno et al. |
| 2014/0155721 A1 | 6/2014 | Hauck et al. |
| 2014/0316297 A1 | 10/2014 | McCaughan et al. |
| 2015/0320515 A1 | 11/2015 | Edwards et al. |

FOREIGN PATENT DOCUMENTS

| | | |
|---|---|---|
| JP | H07-79996 | 3/1995 |
| JP | 2007-021218 A | 2/2007 |
| WO | WO 00/10456 A1 | 3/2000 |
| WO | WO 2012/092016 | 7/2012 |
| WO | WO 2013/154855 | 10/2013 |

OTHER PUBLICATIONS

Office Action for U.S. Appl. No. 13/747,266, dated Jan. 2, 2015.
Office Action for U.S. Appl. No. 13/747,266, dated Jul. 17, 2015.
Office Action for U.S. Appl. No. 13/747,266, dated Jan. 15, 2016, 28 pages.
Office Action for U.S. Appl. No. 13/747,266, dated Aug. 10, 2016.
International Search Report and Written Opinion for International Application No. PCT/US2013/034789, dated Jul. 18, 2013.
Office Action for U.S. Appl. No. 14/802,641, dated May 17, 2016.
International Search Report and Written Opinion for International Application No. PCT/US2015/021435, dated Jun. 10, 2015.
International Search Report and Written Opinion for International Application No. PCT/US2016/044228, dated Dec. 7, 2016, 10 pages.
Brooks, A. G. et al., "Outcomes of Long-Standing Persistent Atrial Fibrillation Ablation: A Systematic Review," Heart Rhythm, 7(6):835-846 (2010).
Calkins, H. et al., "2012 HRS/EHRA/ECAS Expert Consensus Statement on Catheter and Surgical Ablation of Atrial Fibrillation: Recommendations for Patient Selection, Procedural Techniques, Patient Management and Follow-up, Definitions, Endpoints, and Research Trial Design," Eurospace, 14:528-590p (2012).
Cuculich, P. S. et al., "Noninvasive Characterization of Epicardial Activation in Humans With Diverse Atrial Fibrillation Patterns," Circulation, 122(14):1364-1372 (2010) and supplemental materials.
Go, A. S. et al., "Prevalence of Diagnosed Atrial Fibrillation in Adults: National Implications for Rhythm Management and Stroke Prevention: the AnTicoagulation and Risk Factors in Atrial Fibrillation (ATRIA) Study," JAMA, 285(18):2370-2375 (2001).
Haissaguerre, M. et al., "Driver Domains in Persistent Atrial Fibrillation," Circulation, 130:530-538 (2014).
Haissaguerre, M. et al., "Spontaneous Initiation of Atrial Fibrillation by Ectopic Beats Originating in the Pulmonary Veins," N. Engl. J. Med., 339(10):659-666 (1998).
Jadidi, A. S. et al., "Inverse Relationship Between Fractionated Electrograms and Atrial Fibrosis in Persistent Atrial Fibrillation: Combined Magnetic Resonance Imaging and High-Density Mapping," Journal of the American College of Cardiology, 62(9):802-812 (2013).
Miller, J. M. et al., "Initial Independent Outcomes From Focal Impulse and Rotor Modulation Ablation for Atrial Fibrillation: Multicenter FIRM Registry," J. Cardiovasc. Electrophysiol., 25(9):921-929 (2014).
Miyasaka, Y. et al., "Secular Trends in Incidence of Atrial Fibrillation in Olmsted County, Minnesota, 1980 to 2000, and Implications on the Projections for Future Prevalence," Circulation, 114(2):119-125 (2006).
Narayan, S. M. et al., "Treatment of Atrial Fibrillation by the Ablation of Localized Sources: Confirm (Conventional Ablation for Atrial Fibrillation With or Without Focal Impulse and Rotor Modulation) Trial," Journal of the American College of Cardiology, 60(7):628-636 (2012).
Narayan, S. M. et al., "Computational Mapping Identifies Localized Mechanisms for Ablation of Atrial Fibrillation," PLos ONE, 7(9):e46034 (2012), 8 pages.
Pandit, S. V. et al., "Rotors and the Dynamics of Cardiac Fibrillation," Circulation Research, 112(5):849-862 (2013).

(56) References Cited

OTHER PUBLICATIONS

Wilber, D. J. et al., "Comparison of Antiarrhythmic Drug Therapy and Radiofrequency Catheter Ablation in Patients With Paroxysmal Atrial Fibrillation: A Randomized Controlled Trial," JAMA, 303(4):333-340 (2010).

Kurian, Thomas et al., "Identification of drivers in patients with persistent atrial fibrillation using a novel spatiotemporal computational algorithm integrated with electroanatomic mapping," Abstract, The Boston AF Symposium, Apr. 9, 2014 pp. 564-565.

Karthikeyan, Umapathy et al., "Phase Mapping of Cardiac Fibrillation," Circ Arrhythm Electrophysiol, 2010; 3:105-114.

Kremen, V. et al., "Comparison of Several Classifiers to Evaluate Endocardial Electrograms Fractionation in Human," 31st Annual International Conference of the IEEE EMBS, Sep. 2009; 2502-2505.

Final Office Action issued by the United States Patent and Trademark Office for U.S. Appl. No. 14/802,641, dated Mar. 10, 2017, 15 pages.

Advisory Action and After Final Consideration Program Decision issued by The United States Patent and Trademark Office for U.S. Appl. No. 14/802,641, dated Mar. 7, 2018, 9 pages.

Sahakian et al. "Sensing and Documentation of Body Position During Ambulatory ECG Monitoring" Computers in Cardiology 2000; 27:77-80.

Office Action for European Application No. 13775770.4, dated Nov. 17, 2016.

Office Action for European Application No. 13775770.4, dated Aug. 10, 2017, 4 pages.

Notice of Reasons for Rejection for Japanese Application No. 2015-505782, dated Jan. 19, 2017, 9 pages, with English translation.

Office Action issued by the Japanese Patent Office for Application No. 2015505782_dated Oct. 24, 2017, 7 pages, with English translation.

Office Action for European Application No. 13775770.4, dated Jul. 27, 2018, 3 pages.

Non-Final Office Action issued by The United States Patent and Trademark Office for U.S. Appl. No. 14/802,641, dated Oct. 5, 2018, 18 pages.

Office Action for European Application No. 13775770.4, dated Mar. 13, 2019, 4 pages.

METHODS FOR LOCALIZING MEDICAL INSTRUMENTS DURING CARDIOVASCULAR MEDICAL PROCEDURES

PRIORITY

This application is a continuation of U.S. patent application Ser. No. 13/747,266, now U.S. Pat. No. 9,510,772, filed Jan. 22, 2013, entitled "System and Method for Localizing Medical Instruments During Cardiovascular Medical Procedures," which claims priority to and the benefit of U.S. Provisional Patent Application No. 61/622,220, filed Apr. 10, 2012, entitled "Integrated Multi-Localizer Cardiovascular Navigation System and Associated Method," each of which are incorporated herein by reference in their entireties and for all purposes.

FIELD OF THE INVENTION

The present invention relates generally to systems and methods that aid physicians in performing surgical procedures on patients. More specifically, the invention relates to systems and methods for localizing medical instruments within a subject during cardiovascular medical procedures.

BACKGROUND OF THE INVENTION

Medical procedures to treat cardiovascular diseases are becoming less invasive in nature, such that a physician can insert a small medical device into a subject through a small incision and navigate the device through vasculature to the heart and the specific treatment site. One result is that the physician requires specialized tools to see where the device is travelling as well as the destination treatment location. Stereotactic navigation is the field of taking pre-acquired images of the anatomy of interest and using localization systems to track medical instruments with respect to the pre-acquired imaging. Stereotactic navigation requires position sensing capabilities to be able to locate and track the medical instruments within the human body and display the position with respect to other medical imagery like x-ray, CT, MRI, ultrasound, and electrocardiogram maps.

Current position sensing systems suffer from several issues. Position sensing systems need to provide flexibility to localize many different instruments based on physician preference, and accuracy in inhomogeneous tissues such as bone, air, blood, muscle, and fat, as those tissue characteristics change with breathing and heart beat. The balance of accuracy and flexibility is very difficult to achieve. Electromagnetic position sensing systems are often accurate systems because they do not depend on the tissue characteristics of the living body. However, electromagnetic systems are very proprietary in nature and require proprietary electromagnetic sensors embedded in every instrument used during the procedure that the physician needs to localize. Electrical-potential position sensing systems are typically very flexible in their ability to track different instruments in an open architecture manner using standard electrodes integrated into many medical instruments. However, the accuracy of electrical-potential systems is poor because they are susceptible to the varying tissue impedance changes due to breathing and heartbeat.

Attempts to combine the accuracy of electromagnetic localization and flexibility of electrical-potential localization have so far failed to provide a system that overcomes the issues of the separate systems. Current hybrid position sensing systems aim to calibrate a volume localized by electrical-potential localization to a volume localized by electromagnetic localization with a single instrument with respect to body surface electrodes and use that calibration to track other instruments in a common calibrated volume. However, any calibration of electromagnetic localization field to electrical-potential localization field calculated by the single instrument is valid only at a particular point in time correlated with a particular point in a breathing cycle and heart beat cycle or is an average over time that is not particularly accurate at any given single point in time. The result is a gated position sensing system that is only accurate periodically.

Thus, a need exists for improved systems and methods of localizing medical instruments within a subject during minimally invasive cardiovascular medical procedures.

SUMMARY OF THE INVENTION

Illustrative embodiments of the present invention that are shown in the drawings are summarized below. These and other embodiments are more fully described in the Detailed Description section. It is to be understood, however, that there is no intention to limit the invention to the forms described in this Summary of the Invention or in the Detailed Description. One skilled in the art can recognize that there are numerous modifications, equivalents, and alternative constructions that fall within the spirit and scope of the invention as expressed in the claims.

In one illustrative embodiment, a position sensing system comprises an electromagnetic field generator; an antenna reference instrument adapted to be introduced into the heart of a subject, the antenna reference instrument including at least one electromagnetic sensor and at least one electrode; at least one roving instrument adapted to be introduced into the thorax cavity of the subject, the at least one roving instrument including at least one electrode; and a control unit configured to determine position coordinates of the antenna reference instrument based on an electromagnetic signal from the electromagnetic field generator sensed by the at least one electromagnetic sensor; measure an electrical-potential difference between the at least one electrode of the antenna reference instrument and the at least one electrode of the at least one roving instrument; and calibrate the measured electrical-potential difference using the determined position coordinates of the antenna reference instrument to determine position coordinates of the at least one roving instrument.

Another illustrative embodiment is a method for sensing the position of a medical instrument, comprising applying an electromagnetic field to the thorax area of a subject; inserting an antenna reference instrument into the heart of the subject, wherein the antenna reference instrument includes at least one electromagnetic sensor and at least one electrode; inserting at least one roving instrument into the thorax cavity of the subject, wherein the at least one roving instrument includes at least one electrode; determining position coordinates of the antenna reference instrument based on sensing the electromagnetic field using the at least one electromagnetic sensor; measuring an electrical-potential difference between the at least one electrode of the antenna reference instrument and the at least one electrode of the at least one roving instrument; and calibrating the measured electrical-potential difference using the determined position coordinates of the antenna reference instrument to determine position coordinates of the at least one roving instrument.

DETAILED DESCRIPTION OF THE INVENTION

In various illustrative embodiments of the invention, a position sensing system used to navigate medical instruments through a patient's cardiovascular system during a cardiovascular procedure includes an antenna reference instrument that can be inserted into the heart of the patient and localized by at least two different systems. The antenna reference instrument can be inserted into a stable location in the heart by the physician and remain there for the duration of the procedure, providing a stable reference point. This reference point ensures that the images that the physician is viewing during the procedure are accurate. The antenna reference instrument can be localized by an electromagnetic system through its electromagnetic sensor and by an electrical-potential system through its electrodes. The absolute location of the antenna reference instrument is determined by a control unit using an electromagnetic field sensor that is embedded into the antenna reference instrument and the supporting electromagnetic field localization system. The absolute location of the antenna reference instrument is accurate because the electromagnetic system is not dependent on tissue characteristics, the patient's breathing, or the patient's heart beating. Additionally, roving instruments that are used to diagnose diseases and deliver treatments are included. Each roving instrument includes electrodes for localization by the electrical-potential system. Current typical instruments used to diagnose and treat cardiovascular diseases already include electrodes, which makes this a very open-architecture system as it can be used with widely available instruments that are already on the market. The control unit can determine the location of any one of the roving instruments by measuring the electrical-potential difference between the electrodes on the antenna reference instrument and the electrodes on the roving instrument in question. Because the antenna reference instrument location is known and stable, the control unit can calibrate the measurement to determine where the roving instrument is located. The location of the roving instrument is very accurate—even using electrical-potential measurements—because the tissue characteristics that negatively affect those measurements are minimized. Because the roving instrument and antenna reference instruments are in the same tissue, the tissue characteristics can be disregarded, as both instruments are equally affected, and the position location system, in various illustrative embodiments, analyzes the difference between the two.

Figure 1:
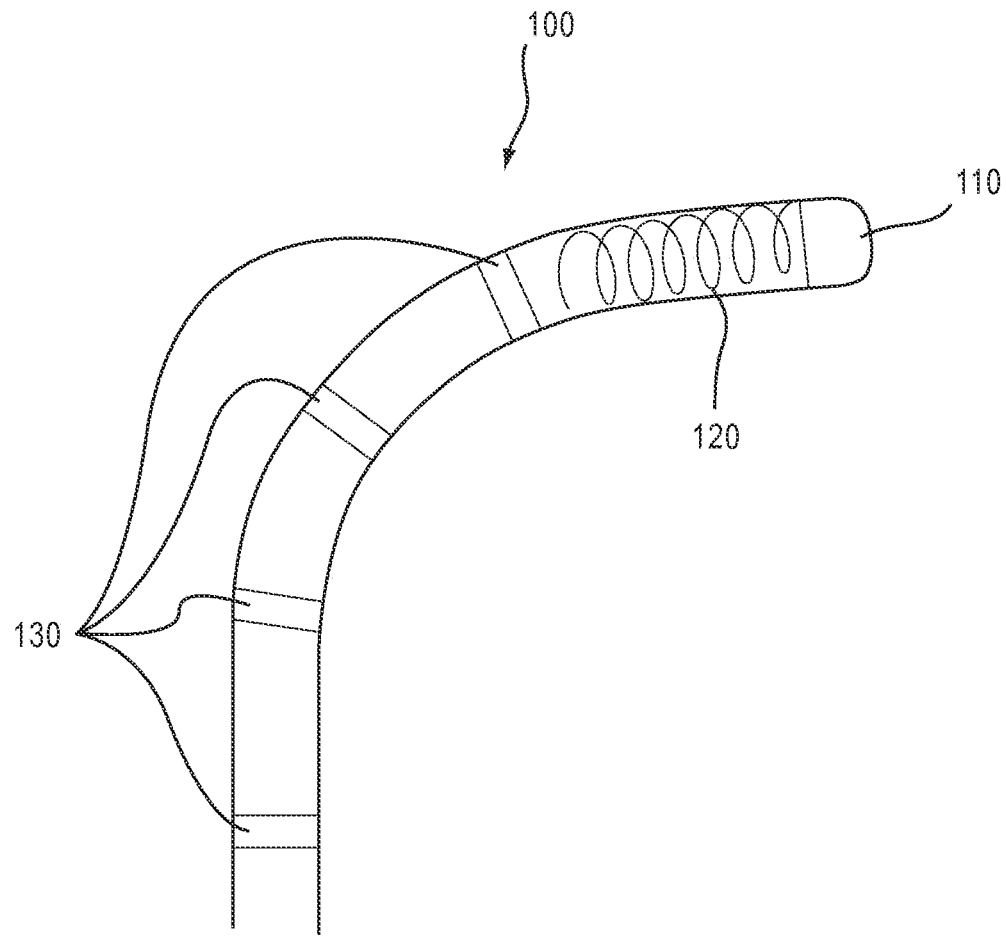
FIG. 1 illustrates an antenna reference instrument, according to an illustrative embodiment of the invention.

Referring now to the drawings, where like or similar elements are designated with identical reference numerals throughout the several views, and referring, in particular, to FIG. 1, it is a schematic illustration of the distal portion of antenna reference instrument 100, in accordance with an illustrative embodiment of the invention. Antenna reference instrument 100 can be any medical instrument that can be adapted to be inserted into the thorax of a subject and is associated with at least two location sensing systems. For example, as shown in FIG. 1, antenna reference instrument 100 can include multiple electrodes 130 for sensing current, voltage, or impedance, as well as electromagnetic sensor 120 for sensing an electromagnetic field. Antenna reference instrument 100 can include a catheter system, a pacemaker lead system, an implantable cardioverter defibrillator lead system, or any other suitable medical device, depending on the particular embodiment.

As stated above, antenna reference instrument 100, in some embodiments, includes a catheter system. In some embodiments, the thickness of the catheter lies in the range of 5 to 7 French. As shown in FIG. 1, the distal end of antenna reference instrument 100 can be curved, although this is not required. In some embodiments, the distal end of antenna reference instrument 100 is fixed, and in other embodiments the distal end of antenna reference instrument 100 has an adjustable deflection.

In some embodiments, distal cap electrode 110 is gold, platinum, silver, or any other suitable material for sensing electrical fields and/or applying electrical energy. Distal cap electrode 110 can be located at the distal tip of antenna reference instrument 100 or any other suitable location near the tip of the distal end of antenna reference instrument 100. In some embodiments, antenna reference instrument 100 does not include distal cap electrode 110. In some embodiments, instead of distal cap electrode 110, antenna reference instrument 100 includes a temporary or permanent pacing lead with fixation devices including, but not limited to, screws or permanent implantation anchors. One benefit of using a more permanent lead device is that, in follow-up procedures, a physician can connect to the already implanted lead, which provides a known location for antenna reference instrument 100.

In some embodiments, multiple electrodes 130 are made from gold, platinum, silver, or any other suitable material for sensing electrical fields. While FIG. 1 depicts four electrodes 130, antenna reference instrument 100 can include any number of electrodes 130. A typical range for the number of electrodes 130 is 1 to 21, though, in some embodiments, more than 20 electrodes can be used. Multiple electrodes 130 can be evenly or unevenly spaced along the catheter, depending on the particular embodiment.

Electromagnetic sensor 120 can be a single coil, as shown in FIG. 1, or electromagnetic sensor 120 can include multiple coils. Electromagnetic sensor 120 can be made of copper, platinum, gold, silver, or any other suitable metal for sensing electromagnetic fields.

In use, antenna reference instrument 100 can be inserted into the heart of a subject. The insertion point can be the femoral artery in the groin area or any suitable insertion point for a cardiovascular procedure on the subject. Once antenna reference instrument 100 is inserted into the heart, electromagnetic sensor 120 senses an electromagnetic field applied, in some embodiments, to the thorax area of the subject. Multiple electrodes 130 can measure current, voltage, or impedance when electrical energy is applied to the thorax area of the subject.

Figure 2:
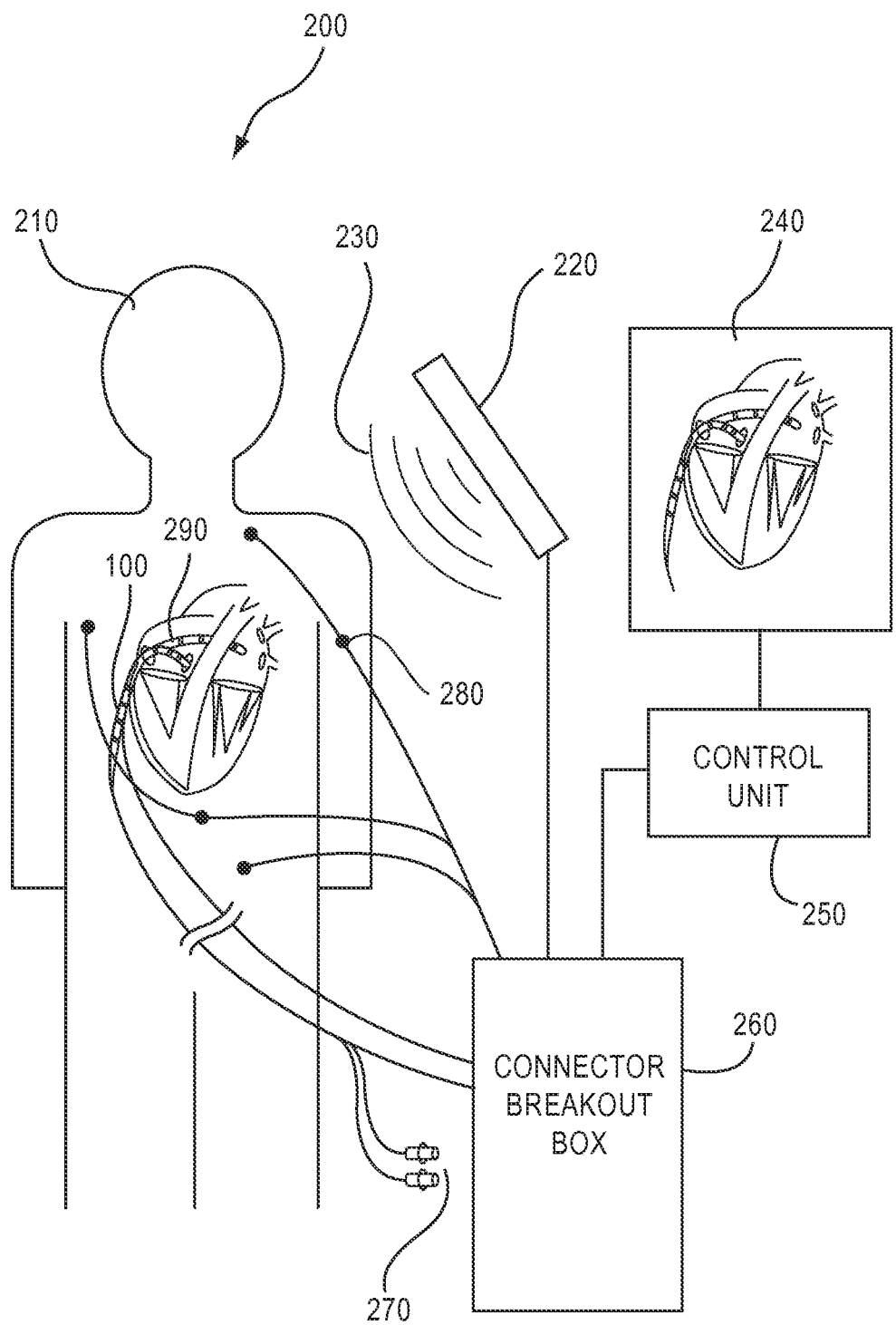
FIG. 2 illustrates a position sensing system, according to an illustrative embodiment of the invention.

FIG. 2 is a depiction of position sensing system 200, according to an illustrative embodiment of the invention. FIG. 2 depicts subject 210, electromagnetic field generator 220, electromagnetic field 230, monitor 240, control unit 250, connector breakout box 260, guiding handles 270, electrical-potential field pads 280, roving instrument 290, and antenna reference instrument 100. In some embodiments, position sensing system 200 is used in a cardiovascular cathlab or operating theatre where other medical instruments, devices, and systems may be present and/or used.

Subject 210 can include a human, animal, or any other suitable subject having a heart.

Electromagnetic field generator 220 emits electromagnetic field 230. In some embodiments, electromagnetic field generator 220 is aligned near subject 210 such that electromagnetic field 230 emitted from electromagnetic field generator 220 engulfs the thorax area of subject 210.

As shown in FIG. 2, monitor 240, in some embodiments, displays a graphical representation of the heart as it beats in subject 210. Monitor 240 can display where roving instrument 290 and antenna reference instrument 100 are located within subject 210 in relation to the subject's heart. Monitor 240 can be configured to display the subject's heart as it beats (dynamically), statically, or not to show the subject's heart at all. Monitor 240 can be configured to display antenna reference instrument 100 alone, in relation to the subject's heart, in relation to one or more roving instruments 290, in relation to both the subject's heart and one or more roving instruments 290, or not at all. Monitor 240 can be configured to display roving instrument 290 alone, in relation to the subject's heart, in relation to antenna reference instrument 100, in relation to other roving instruments 290, in relation to the subject's heart and/or one or more other roving instruments 290 and/or antenna reference instrument 100, or not at all. In some embodiments, position sensing system 200 includes multiple roving instruments 290, which can also be displayed on monitor 240 in any of the combinations described above.

Monitor 240 can be any suitable monitor for displaying static or dynamic images. In some embodiments, position sensing system 200 may not include monitor 240. In other embodiments, position sensing system 200 can include multiple monitors 240.

In some embodiments, monitor 240 can be a touchscreen such that monitor 240 can receive input via options displayed on the screen, allowing the operator to choose the desired display configuration.

Control unit 250 can be connected to monitor 240 and connector breakout box 260, as shown in FIG. 2. Control unit 250 is described in more detail below in connection with FIG. 3.

As shown in FIG. 2, in some embodiments, connector breakout box 260 is connected to control unit 250, electromagnetic field generator 220, electrical-potential field pads 280, roving instrument 290, and antenna reference instrument 100. In other embodiments, connector breakout box 260 can also be connected to other devices and instruments that are used for the procedure. For instance, connector breakout box 260 can be connected to an RF generator, an ultrasound imaging device, an esophageal temperature probe, an electrocardiogram recording device, an x-ray device, a Computed Tomography ("CT") device, a Magnetic Resonance Imaging ("MRI") device, a Positron Emission Tomography ("PET") device, an Optical Coherence Tomography ("OCT") device, and/or any other device used for the procedure.

As shown in FIG. 2, antenna reference instrument 100 can be a device, the distal end of which can travel through the artery system of subject 210 into the heart while navigation handle 270 remains outside subject 210. The physician can use navigation handle 270 to guide the distal end of antenna reference instrument 100 to the desired location within subject 210. The usable length of antenna reference instrument 100 is typically 65 to 110 centimeters, in some embodiments, although in other embodiments antenna reference instrument 100 may be longer than 110 centimeters or shorter than 65 centimeters. As shown in FIG. 1, antenna reference instrument 100 can have multiple sensors, such as one or more electromagnetic sensors 120 and one or more electrodes 130.

As shown in FIG. 2, roving instrument 290 can also include navigation handle 270, which can remain outside subject 210. The physician can use navigation handle 270 to guide the distal end of roving instrument 290 to the desired location within subject 210. Roving instrument 290 can include at least one electrode for sensing current, voltage, or impedance within subject 210. While a single roving instrument 290 is shown in FIG. 2, multiple roving instruments 290 may be used in some embodiments.

Electrical-potential field pads 280 can be placed on the surface of subject 210. FIG. 2 depicts five electrical-potential field pads 280, however there may be more or fewer than five. Electrical-potential field pads 280 generate electrical current through subject 210, which generates electrical fields that can be sensed by electrodes 130 on antenna reference instrument 100 and the electrodes on roving instrument 290. Electrical-potential field pads 280 can be placed on subject 210 such that the electrical fields generated engulf the thorax area of subject 210. For example, electrical-potential field pads 280 can send current through subject 210 from right armpit to left armpit, neck to groin, and front to back such that there is an effective X,Y,Z coordinate system of electrical current running through subject 210.

In use, according to one embodiment, control unit 250 can instruct electromagnetic field generator 220 through connector breakout box 260 to generate electromagnetic field 230 that engulfs the thorax area of subject 210. Control unit 250 can instruct electrical-potential field pads 280 to generate an electrical current through the thorax area of subject 210, as described above.

Electromagnetic sensor 120 in antenna reference instrument 100 can sense electromagnetic field 230, and electromagnetic sensor 120 can send a signal to control unit 250 through connector breakout box 260. Control unit 250 can determine position coordinates of antenna reference instrument 100 based on the signal from electromagnetic sensor 120 in antenna reference instrument 100. Measurements taken from the electromagnetic localization system can be taken in millimeters. In some embodiments, three-dimensional minimum and maximum locations can also be calculated and recorded. Though antenna reference instrument 100 is in a stable location—often the coronary sinus, but antenna reference instrument 100 may also be located in the fossa ovalis, high right atrium, right ventricular apex, or any other stable location—some movement of antenna reference instrument 100 is normal because of blood flow, heartbeat, and breathing of the subject. The minimum and maximum thresholds can be any number, but the movement typically does not exceed 1 centimeter.

Electrodes 130 in antenna reference instrument 100 can measure the impedance, voltage, and/or current generated by electrical-potential field pads 280. Electrodes 130 can send an electrical-impedance and/or electrical-potential value to control unit 250 through connector breakout box 260. Control unit 250 can determine position coordinates of antenna reference instrument 100 based on the electrical-impedance and/or electrical-potential value. In some embodiments, control unit 250 determines absolute position coordinates of antenna reference instrument 100 using electrical-potential.

The electrodes in roving instrument 290 are used to measure the impedance, voltage, and/or current generated by electrical-potential field pads 280. The electrodes permit control unit 250, through connector breakout box 260, to determine a value for the measured electrical impedance and/or electrical potential. In some embodiments, control unit 250 measures the electrical-potential difference and/or the electrical-impedance difference between that measured at antenna reference instrument 100 and that measured at roving instrument 290. Based on the measured difference, control unit 250 can calibrate the measured difference using the determined position coordinates of antenna reference instrument 100 and determine the position coordinates of roving instrument 290.

Control unit 250 can convert the position coordinates for antenna reference instrument 100 and roving instrument 290 into an image to be displayed on monitor 240.

Figure 3:
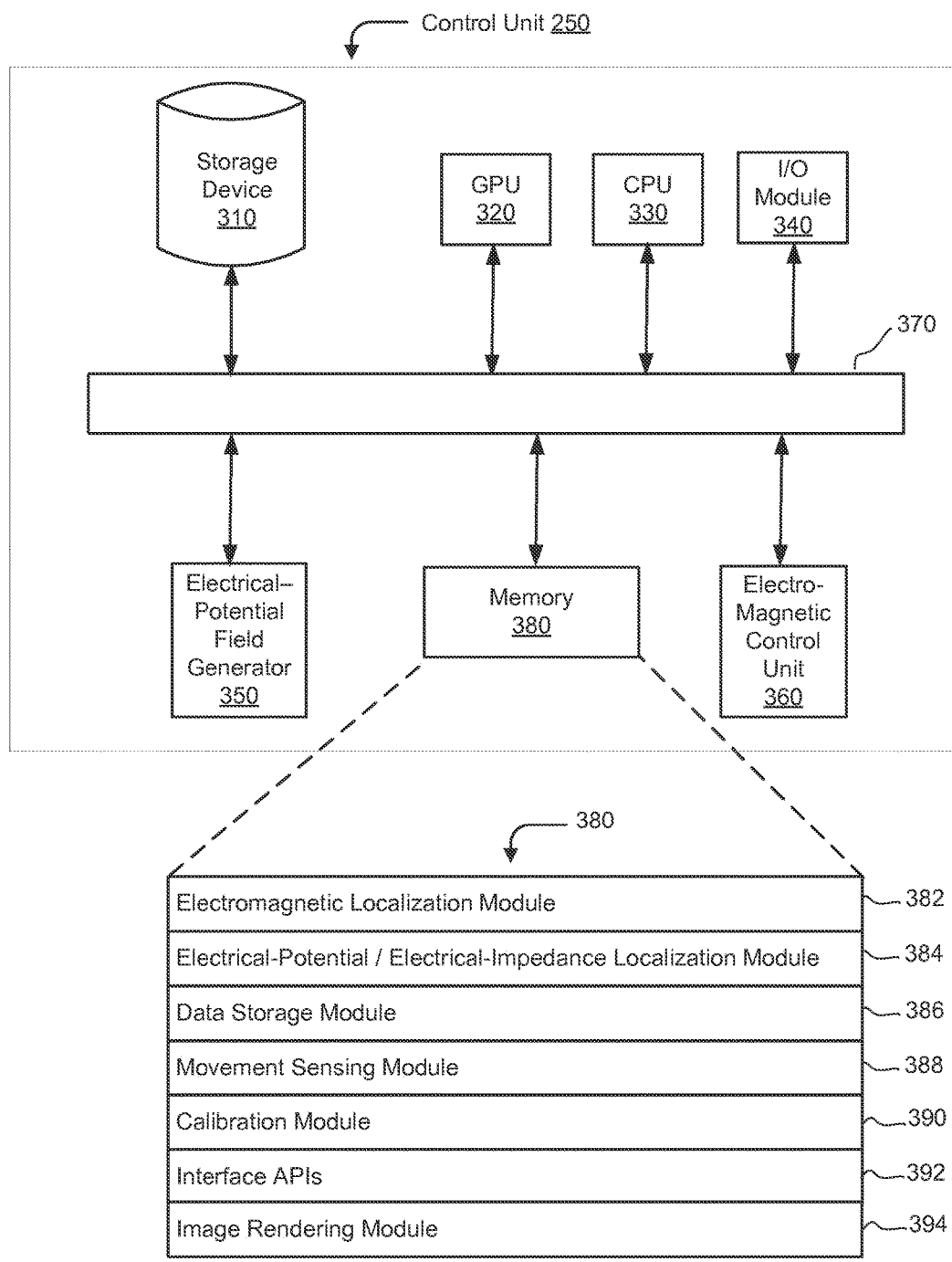
FIG. 3 is a functional block diagram of a control unit for use in a position sensing system, according to an illustrative embodiment of the invention.

FIG. 3 is a functional block diagram of a computerized control unit 250, according to an illustrative embodiment of the invention. In FIG. 3, CPU 330 and GPU 320 communicate over data bus 370 with each other, I/O module 340, storage device 310, electrical-potential field generator 350, electromagnetic control unit 360, and memory 380. While FIG. 3 depicts only a single CPU, multiple CPUs, a multi-core CPU, or multiple multi-core CPUs may be present in some embodiments. Similarly, though a single GPU is depicted in FIG. 3, multiple GPUs, multi-core GPUs, or multiple multi-core GPUs may be present in some embodiments. In some embodiments, CPU 330 and GPU 320 can be configured to process instructions in parallel.

Storage device 310 can include, for example, hard disk drives, storage arrays, network-attached storage, tape-based storage, optical storage, flash-memory-based storage, or any other suitable storage device for use in a computer system. While FIG. 3 depicts a single storage device 310, multiple storage devices may be present in some embodiments.

I/O Module 340 facilitates communication with external devices that communicate with control unit 250. For example, I/O module 340 can facilitate communication with monitor 240 or connector breakout box 260.

In some embodiments, electrical-potential field generator 350 is a module in control unit 250 that controls electrical-potential field pads 280. For example, electrical-potential field generator 350 can control the current flowing through the subject between electrical-potential field pads 280, which generates an electrical-potential field in subject 210. In an illustrative embodiment, electrical-potential field generator 350 can create three separate signals, distinguishable by some characteristic such as frequency, phase, or time so that an X, Y, and Z signal can be separated out to determine position coordinates of the sensing electrode.

Electromagnetic control unit 360 can be a module in control unit 250 that controls electromagnetic field generator 220. Electromagnetic control unit 360 can control the intensity of electromagnetic field 230, as well as turn electromagnetic field generator 220 on and off.

Memory 380 may include, without limitation, random access memory ("RAM"), read-only memory ("ROM"), or flash memory. While FIG. 3 shows a single memory, in some embodiments multiple memory devices including combinations of types may be used. In one embodiment, as shown in FIG. 3, memory 380 includes executable program instructions conceptualized as functional modules, including electromagnetic localization module 382, electrical-potential/electrical-impedance localization module 384, data storage module 386, movement sensing module 388, calibration module 390, interface APIs 392, and image rendering module 394. In other embodiments, the program instructions may be divided into more or fewer modules, and the functional boundaries among the modules can differ from what is indicated in FIG. 3.

Electromagnetic localization module 382 determines position coordinates of instruments, including antenna reference instrument 100, that include electromagnetic sensor 120. In some embodiments, electromagnetic localization module 382 converts the signals from electromagnetic sensor 120 into X, Y, and Z position coordinates.

Electrical-potential/electrical-impedance localization module 384 determines position coordinates of instruments, including antenna reference instrument 100 and roving instruments 290, that include one or more electrodes 130. In some embodiments, electrical-potential/electrical-impedance localization module 384 converts the signals from electrode 130 into X, Y, and Z position coordinates.

Data storage module 386 controls the storage of data, including, without limitation, position coordinates or images and data from the many devices that I/O module 340 communicates with, as described above.

Movement sensing module 388 recognizes movement of antenna reference instrument 100 beyond the predetermined threshold described above. In some embodiments, if antenna reference instrument 100 moves, the physician can be notified through a visual or audio alert. The physician can move antenna reference instrument 100 back to the stable location within the predetermined threshold. In some embodiments, the new location of antenna reference instrument 100 can be used, and an offset can be applied to recalibrate the stored images and data for accurate display of the locations of antenna reference instrument 100 and roving instrument 290.

Calibration module 390 calibrates the measured differences in electrical-potential or electrical-impedance between antenna reference instrument 100 and roving instrument 290. Within the calibration module 390, various mathematical operations are performed. In some embodiments, a three-space coordinate system can be created with voltage values in each orthogonal (anterior-posterior, inferior-superior, and laterally) axis. For example, electrical-potential field pads 280 can send electrical current through subject 210 from right armpit to left armpit, neck to groin, and front to back such that there is an effective X, Y, Z coordinate system of electrical current running through subject 210. Each axis can have a different carrier frequency. In one embodiment, the X-axis frequency is 30 kHz, the Y-axis frequency is 31 kHz, and the Z-axis frequency is 32 kHz, although other carrier frequencies can be used. A composite voltage can be measured as a difference between an electrode on roving instrument 290 and an electrode 130 on antenna reference instrument 100. A Fourier transformation can be performed on the composite voltage to extract the separate X, Y, and Z voltage measurements corresponding to the X, Y, Z coordinate system. These real-time X, Y, and Z voltage measurements can be placed into a memory buffer and averaged over varying periods of time to smooth out any inherent noise in the system and provide the operator with various levels of sensitivity of roving-instrument motion, depending on the operator's haptic preference.

Similarly, in some embodiments, electrical-impedance differences are measured between an electrode on roving instrument 290 and an electrode 130 on antenna reference instrument 100. A Fourier transformation can be performed on the composite impedance measurement to extract the separate X, Y, and Z impedance measurements corresponding to the X, Y, Z coordinate system created by the electrical-potential field pads 280. Buffering and smoothing calculations can be performed to ensure noise cancellation and varying levels of roving instrument motion feedback.

Interface APIs 392 provide interfaces between control unit 250 and other devices, including, without limitation, an x-ray device, an RF generator, an ultrasound imaging device, an esophageal temperature probe, an electrocardiogram recording device, a Computed Tomography ("CT") device, a Magnetic Resonance Imaging ("MRI") device, a Positron Emission Tomography ("PET") device, an Optical Coherence Tomography ("OCT") device, and/or any other device used in a cardiovascular procedure.

Figure 4A:
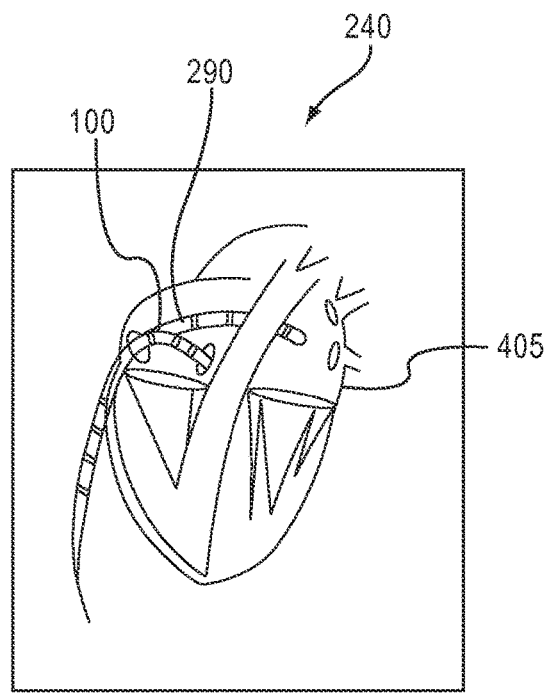
FIG. 4a illustrates a display for tracking instruments relative to a subject's heart, according to an illustrative embodiment of the invention.

FIG. 4a is an illustration, according to an illustrative embodiment of the invention, of monitor 240. Monitor 240 includes a rendered image of antenna reference instrument 100, the subject's heart 405, and roving instrument 290.

In some embodiments monitor 240 can display the heart dynamically such that the subject's heart 405 is shown as beating on monitor 240 substantially in time with the subject's true heartbeat. Monitor 240 can also display the movement of roving instrument 290 in substantially real-time as the physician moves roving instrument 290. The rendered image of antenna reference instrument 100 can also be shown in substantially real-time.

As described above, monitor 240 can be any suitable display monitor for use with a computer system, including without limitation a CRT, a touchscreen, an LCD, a plasma, or an LED display.

Figure 4B:
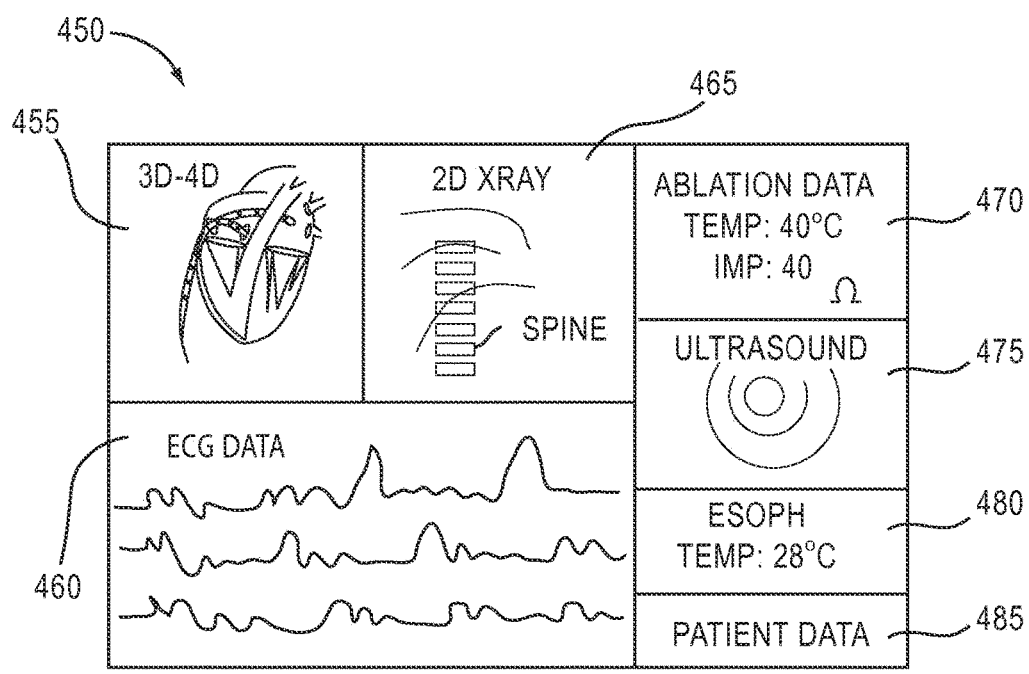
FIG. 4b illustrates a display for tracking instruments relative to a subject's heart, according to another illustrative embodiment of the invention.

FIG. 4b is an illustration, according to another illustrative embodiment, of monitor 450. In this embodiment, the images displayed include not only the subject's heart in the heart display 455, but also include ECG data display 460, x-ray display 465, ablation data display 470, ultrasound display 475, esophageal data display 480, and other patient data display 485.

In one embodiment, the data displays described above are all updated by control unit 250. For example, as control unit 250, via Interface APIs 392, communicates with external devices such as the ultrasound imaging device and receives updated imaging information, GPUs 320 render the images and send the rendered images via I/O module 340 to ultrasound data display 475 on monitor 450.

Figure 5:
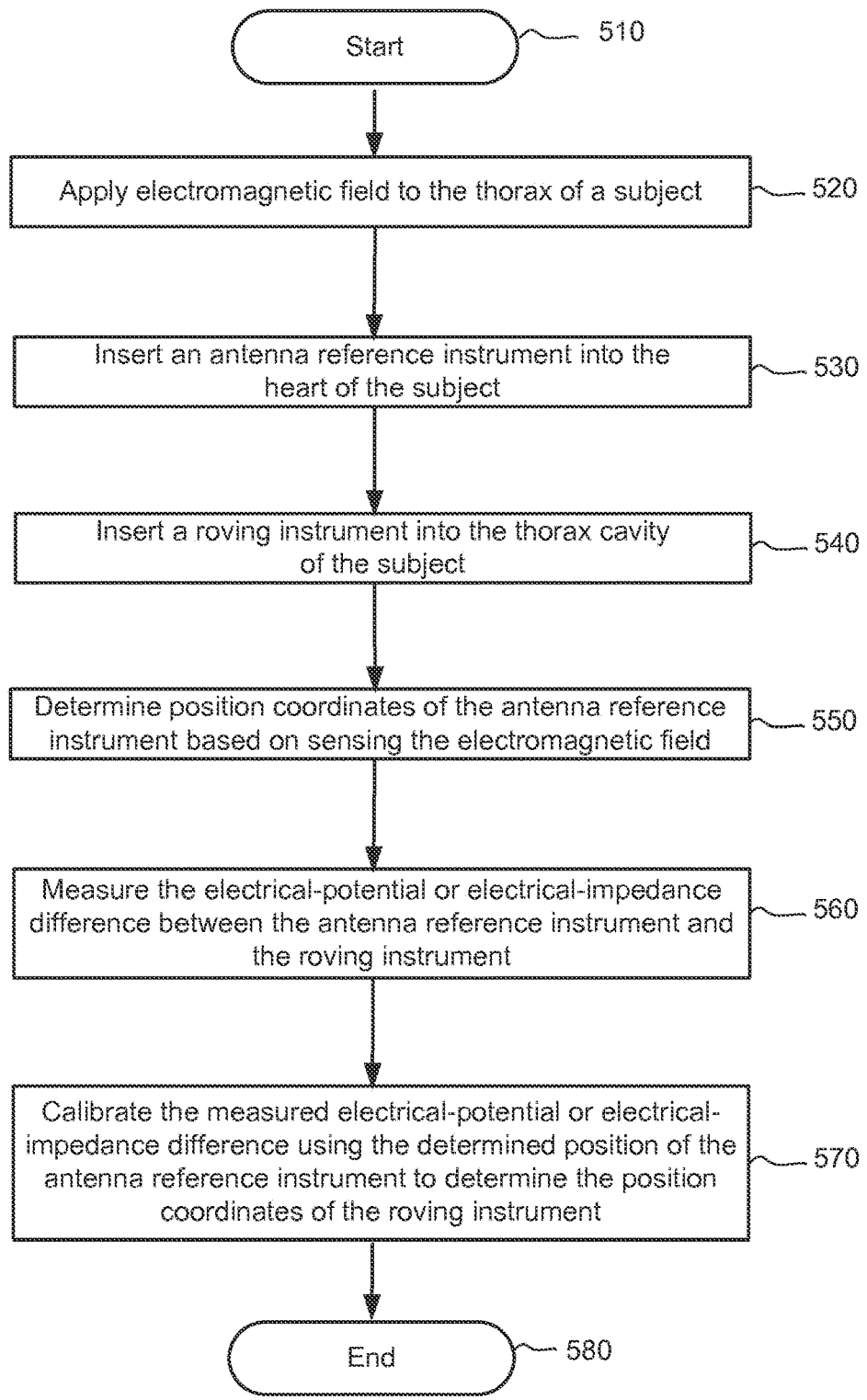
FIG. 5 is a flowchart of a method for determining the position of a roving instrument, according to an illustrative embodiment of the invention.

FIG. 5 is a flowchart of a method for determining the position coordinates of roving instrument 290 in accordance with an illustrative embodiment of the invention. At 520, electromagnetic field 230 is applied to the thorax of a subject. In some embodiments, electromagnetic control unit 360 in control unit 250 sends a signal to electromagnetic field generator 220 that causes electromagnetic field generator 220 to emit electromagnetic field 230.

At 530, antenna reference instrument 100 is inserted into the heart of the subject. In some embodiments, the insertion point is the femoral artery in the groin area of the subject. From there, antenna reference instrument 100 is guided through the vasculature to the subject's heart.

At 540, roving instrument 290 is inserted into the thorax cavity of the subject. In some embodiments, the insertion point is the same as the insertion point for antenna reference instrument 100. However, the insertion point can include any suitable insertion point that allows access to the thorax cavity of the subject.

At 550, position coordinates of antenna reference instrument 100 are determined based on sensing electromagnetic field 230. In some embodiments, electromagnetic sensor 120 in antenna reference instrument 100 detects electromagnetic field 230 that was applied to the thorax area of the subject at 520. The electromagnetic sensor 120 conveys a signal to control unit 250. Electromagnetic localization module 382 interprets the signal and converts the signal into position coordinates of antenna reference instrument 100.

At 560, the electrical-potential and/or electrical-impedance difference between antenna reference instrument 100 and roving instrument 290 is measured. The electrodes 130 in antenna reference instrument 100 and the electrodes in roving instrument 290 each convey a signal to control unit 250. Electrical-potential/electrical-impedance localization module 384 interprets the signal and measures the electrical-potential and/or the electrical-impedance difference.

At 570, the position coordinates of roving instrument 290 are determined by calibrating the electrical-potential difference or the electrical-impedance difference between antenna reference instrument 100 and roving instrument 290 using the determined position coordinates of antenna reference instrument 100. Calibration module 390 uses the position coordinates of antenna reference instrument 100 determined at 550 and the measured electrical-potential and/or electrical-impedance difference measured at 560 to calibrate the difference and determine the position coordinates of roving instrument 290.

Figure 6:
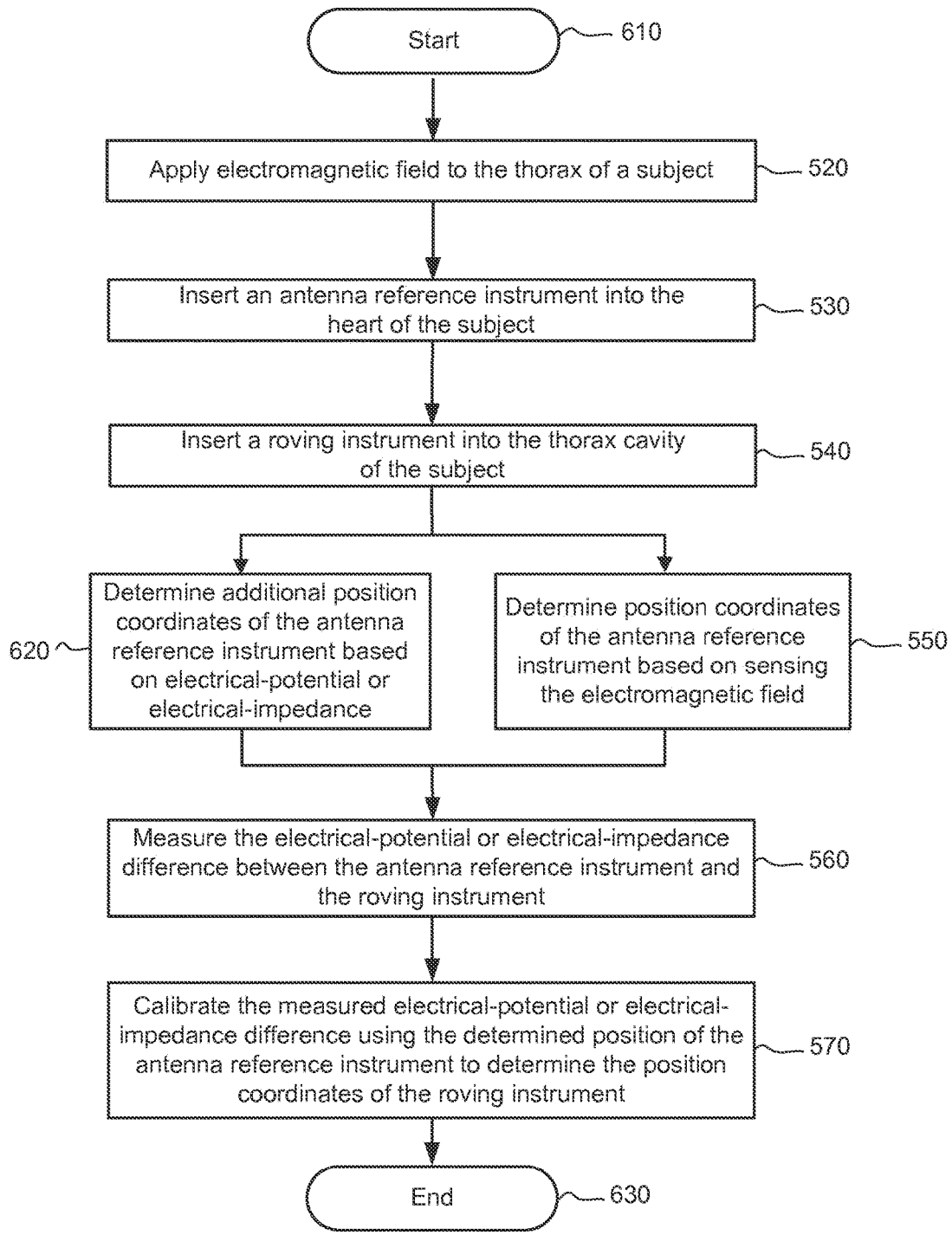
FIG. 6 is a flowchart of a method for determining the position of a roving instrument, according to another illustrative embodiment of the invention.

FIG. 6 is a flowchart of a method for determining the position coordinates of roving instrument 290 in accordance with an illustrative embodiment of the invention. As in the embodiment discussed in connection with FIG. 5, Blocks 520-570 are preformed. In some embodiments, at 620 additional position coordinates of antenna reference instrument 100 are determined in parallel with Block 550. This can provide redundant absolute location tracking of antenna reference instrument 100. At 620, electrodes 130 in antenna reference instrument 100 convey a signal to control unit 250. Electrical-potential/electrical-impedance localization module 384 interprets the signal and converts it into position coordinates of antenna reference instrument 100.

Figure 7:
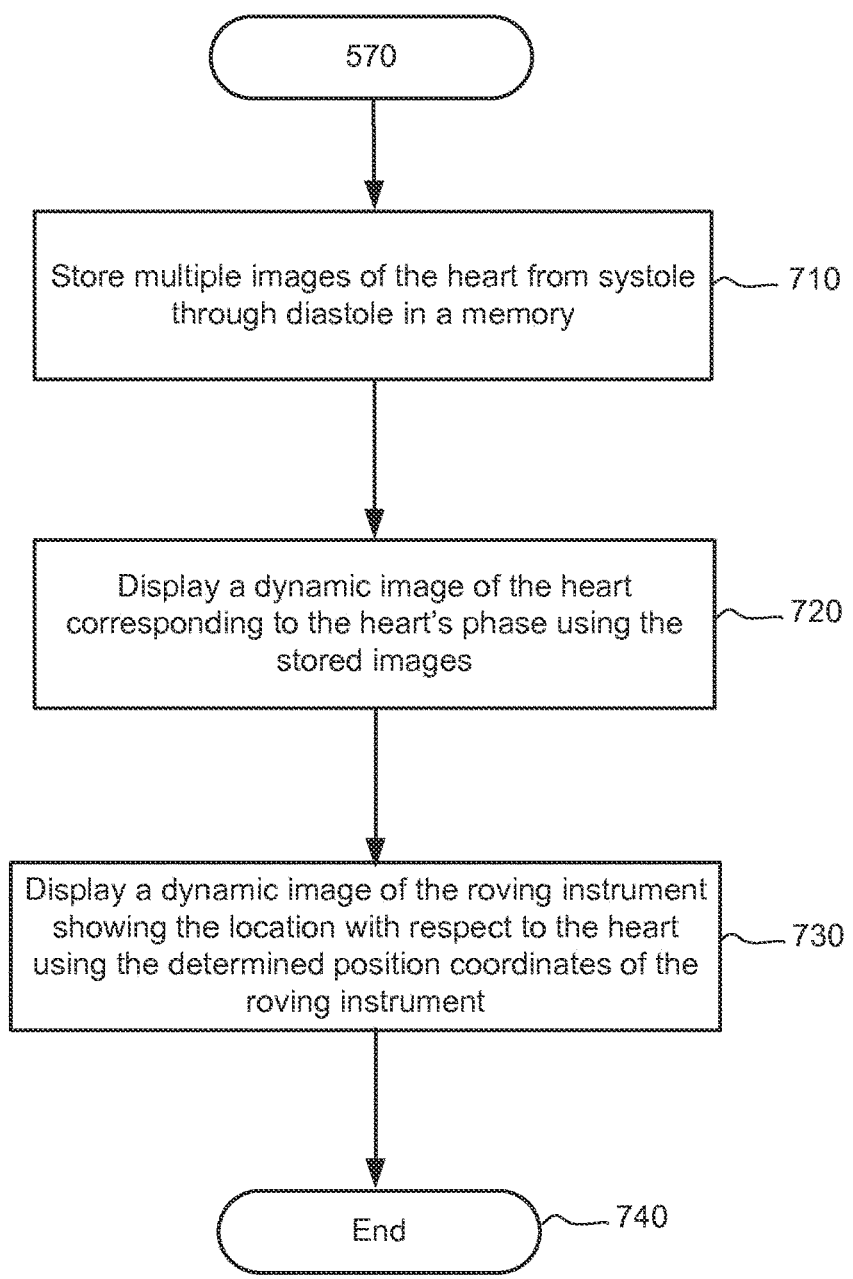
FIG. 7 is a flowchart of a method for displaying the position of a roving instrument, according to yet another illustrative embodiment of the invention.

FIG. 7 is a flowchart of a method for displaying dynamic images of the localized instruments in accordance with an illustrative embodiment of the invention. Starting from Block 570 in FIG. 5 or FIG. 6, at 710, multiple images of the heart from systole through diastole are stored in a memory. The images may be captured from any of the external devices that communicate with control unit 250. For example, the images can be captured from an ultrasound imaging device, an x-ray device, an MRI device, and/or any other imaging device. Once captured by control unit 250, data storage module 386 stores the images on storage device 310.

At 720, the dynamic images of the heart are displayed on monitor (240, 450) corresponding to the subject's heart's phase, such that the images are displayed in substantially real-time with the beating heart of the subject. Image rendering module 394 utilizes GPU 320 to render images for display on monitor (240, 450) and correlates the display to occur in substantially real-time with the heart's phase by utilizing input from the external devices that provide data indicating the phase of the heart, such as ECG data.

At 730, the roving instrument image is also rendered on monitor (240, 450), in this embodiment. Image rendering module 394 utilizes GPU 320 to render images for display on monitor (240, 450) and correlates the display to occur in substantially real-time as roving instrument 290 moves.

Figure 8:
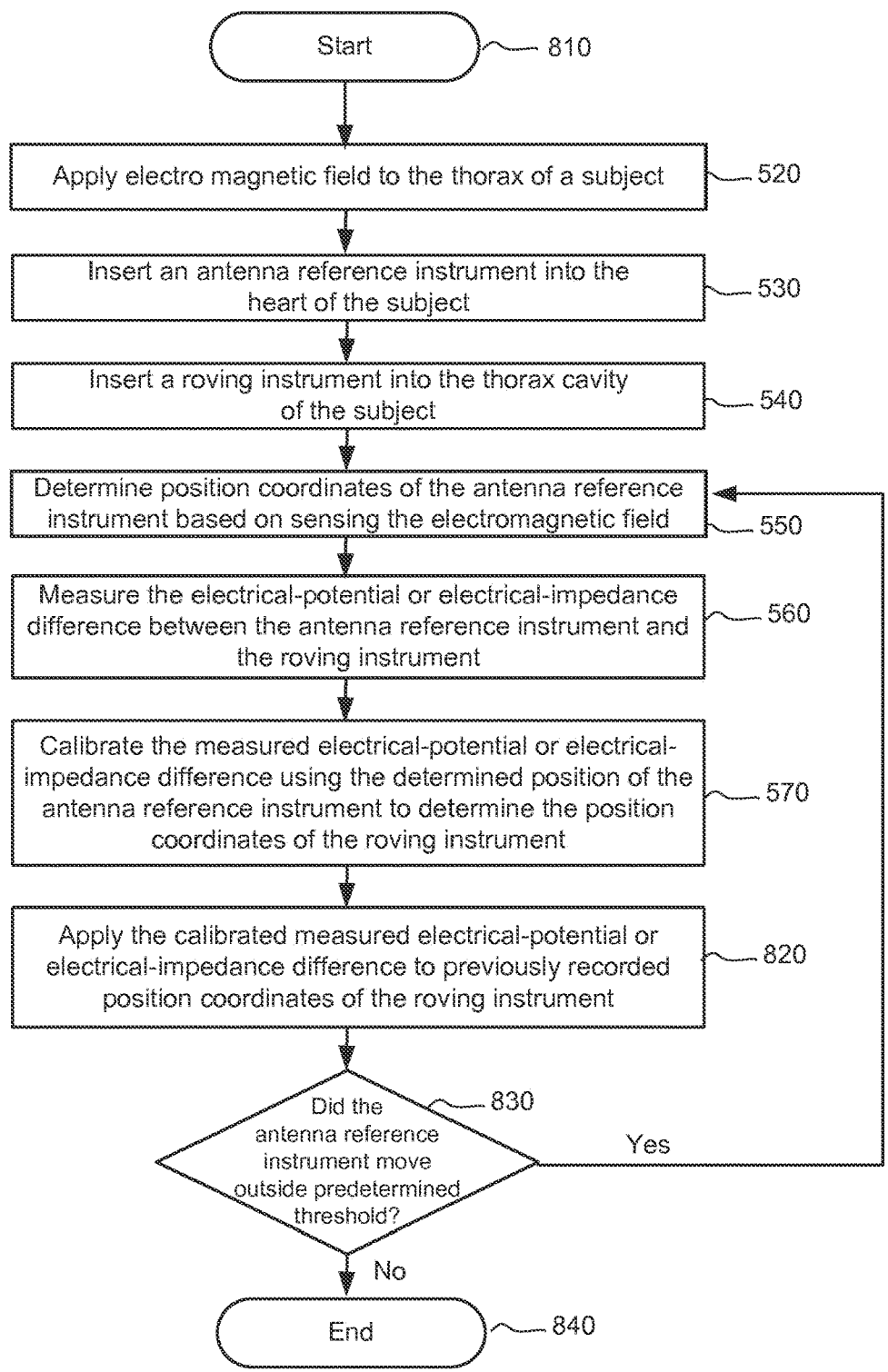
FIG. 8 is a flowchart of a method for determining the position of a roving instrument, according to yet another illustrative embodiment of the invention.

FIG. 8 is a flowchart of a method for correcting the display if antenna reference instrument 100 moves outside of a predetermined threshold, in accordance with an illustrative embodiment. In this embodiment, Blocks 520, 530, 540, 550, 560, and 570 remain the same as in FIGS. 5 and 6. At 820, the calibrated measured electrical-potential and/or electrical-impedance difference is applied to previously recorded position coordinates of roving instrument 290. Calibration module 390 can check for previously recorded position coordinates of roving instrument 290 and apply the calibration such that when the image of roving instrument 290 is rendered, it appears in the proper position because the position coordinates are properly calibrated in reference to antenna reference instrument 100.

At 830, the location of antenna reference instrument 100 is checked to determine whether it moved outside a predetermined threshold. If antenna reference instrument 100 moved sufficiently, the method returns to Block 550 and determines the new position coordinates of antenna reference instrument 100 based on sensing electromagnetic field 230 through electromagnetic sensor 120 in antenna reference instrument 100. In some embodiments, the position of antenna reference instrument 100 is tracked redundantly using both electromagnetic and electrical-potential positioning techniques. As described above, a predetermined threshold can be chosen because the beating of the subject's heart as well as the subject's breathing will cause antenna reference instrument 100 to move approximately 1 centimeter, which is considered normal. However, if antenna reference instrument 100 slips from its substantially stable location, the rendered images of roving instrument 290 will no longer be accurate without a recalibration. Once antenna reference instrument 100 moves, an offset can be applied to calibrate all the images to the new antenna reference instrument 100 location, allowing all location data to be accurate as displayed on monitor (240, 450). In this manner, shifts in position of antenna reference instrument 100 during the procedure can be compensated for.

While various embodiments have been described above, it should be understood that they have been presented by way of example only, and not limitation. Where methods and/or flowcharts described above indicate certain events and/or flow patterns occurring in a certain order, the ordering of certain events and/or flow patterns may be modified. While the embodiments have been particularly shown and described, it will be understood that various changes in form and details may be made.

For instance, in some embodiments multiple roving instruments may be used. In those embodiments, multiple measurement steps can be done to determine each roving instrument's location. Those measurement steps can be done in parallel, but they need not be done in parallel, depending on the embodiment.

Although various embodiments have been described as having particular features and/or combinations of components, other embodiments are possible having a combination of any features and/or components from any of the embodiments as discussed above. For example, while electromagnetic and electrical-potential or electrical-impedance localization methods were used throughout this disclosure, any combination of those systems may be used. Additionally, other types of localization systems could be used.

In conclusion, the present invention provides, among other things, systems and methods for localizing medical instruments within a subject during cardiovascular medical procedures. Those skilled in the art can readily recognize that numerous variations and substitutions may be made in the invention, its use, and its configuration to achieve substantially the same results as achieved by the embodiments described herein. Accordingly, there is no intention to limit the invention to the disclosed exemplary forms. Many variations, modifications, and alternative constructions fall within the scope and spirit of the disclosed invention as expressed in the claims.

What is claimed is:

1. A method, comprising:
   (a) determining at a first time a first position coordinate of an antenna reference instrument based on sensing an electromagnetic field using an electromagnetic sensor, the electromagnetic field being applied to a thorax area of a subject, a distal portion of the antenna reference instrument (1) including the electromagnetic sensor and an electrode, and (2) being minimally invasively delivered to and disposed in a living coronary sinus of a living heart of the subject during the determining at the first time;
   (b) determining at a second time after the first time a second position coordinate of the antenna reference instrument based on sensing the electromagnetic field using the electromagnetic sensor;
   (c) identifying a shift of the antenna reference instrument based on comparing the first position coordinate to the second position coordinate;
   (d) measuring an electrical-potential difference between the electrode of the antenna reference instrument and an electrode of a roving instrument that is disposed in a thorax cavity of the subject; and
   (e) in response to identifying the shift of the antenna reference instrument, determining a position coordinate of the roving instrument based on the measured electrical-potential difference and the second position coordinate of the antenna reference instrument.

2. The method of claim 1, wherein the distal portion of the antenna reference instrument has an adjustable deflection.

3. The method of claim 1, wherein the antenna reference instrument includes at least one of a pacemaker or an implantable cardioverter defibrillator lead system designed for placement in and cannulation of the living coronary sinus.

4. The method of claim 1, further comprising:
   displaying, before the identifying the shift, a first image of the living heart with a representation of the roving instrument disposed therein, the first image being based on the first position coordinate of the antenna reference instrument; and
   displaying, after the identifying, a second image of the living heart with a representation of the roving instrument disposed therein, the second image being based on the second position coordinate of the antenna reference instrument and the calibrating the measured electrical-potential difference, the second image being different from the first image.

5. The method of claim 1, wherein the distal end portion of the antenna reference instrument is delivered to and disposed in the living coronary sinus with a catheter system designed for placement in and cannulation of the living coronary sinus.

6. The method of claim 5, wherein the catheter system has a usable length of about 65-110 centimeters, a thickness of about 507 French, and an adjustable deflection in the range of at least 0-180 degrees, the catheter system including 2-20 electrodes for sensing electrocardiograms and an integrated electromagnetic sensor that includes at least one metallic coil.

7. The method of claim 1, wherein at least one of an audio alert or a visual alert is generated in response to the identifying the shift.

8. A method, comprising:
(a) identifying at a first time a shift of an antenna reference instrument based on comparing (i) a position of the antenna reference instrument determined using an electromagnetic sensor that is coupled to a distal portion of the antenna reference instrument to (ii) a position of the antenna reference instrument determined using the electromagnetic sensor at a second time after the first time, when an electromagnetic field is applied to a thorax area of a subject and the distal portion of the antenna reference instrument is disposed in a living coronary sinus of a living heart of the subject;
(b) measuring an electrical-potential difference between an electrode that is coupled to the distal portion of the antenna reference instrument and an electrode that is coupled to a roving instrument that is disposed in a thorax cavity of the subject; and
(c) in response to identifying the shift of the antenna reference instrument, determining a position of the roving instrument based on the measured electrical-potential different and the position of the antenna reference instrument determined using the electromagnetic sensor at the second time.

9. The method of claim 8, wherein the distal portion of the antenna reference instrument is configured to be adjustably deflected.

10. The method of claim 8, wherein the antenna reference instrument includes at least one of a pacemaker or an implantable cardioverter defibrillator lead system designed for placement in and cannulation of the living coronary sinus.

11. The method of claim 8, further comprising:
displaying, before the identifying the shift, a first image of the living heart with a representation of the roving instrument disposed therein, the first image being based on the position of the antenna reference instrument determined using the electromagnetic sensor at the first time; and
displaying, after the identifying, a second image of the living heart with a representation of the roving instrument disposed therein, the second image being based on the position of the antenna reference instrument determined using the electromagnetic sensor at a second time and the calibrating the measured electrical-potential difference, the second image being different from the first image.

12. The method of claim 8, wherein the distal end portion of the antenna reference instrument is delivered to and disposed in the living coronary sinus with a catheter system designed for placement in and cannulation of the living coronary sinus.

13. The method of claim 12, wherein the catheter system has a usable length of about 65-110 centimeters, a thickness of about 507 French, and is configured to be deflected in the range of at least 0-180 degrees, the catheter system including 2-20 electrodes for sensing electrocardiograms and an integrated electromagnetic sensor that includes at least one metallic coil.

14. The method of claim 8, wherein at least one of an audio alert or a visual alert is generated in response to the identifying the shift.

* * * * *